US010106766B2

(12) United States Patent
Lee et al.

(10) Patent No.: US 10,106,766 B2
(45) Date of Patent: Oct. 23, 2018

(54) MICROFLUIDIC BIO-REACTOR DEVICE

(71) Applicant: NATIONAL YANG-MING UNIVERSITY, Taipei (TW)

(72) Inventors: Oscar Kuang-Sheng Lee, Taipei (TW); Meng-Hua Yen, Taipei (TW); Shu-Wen Kuo, Taipei (TW)

(73) Assignee: NATIONAL YANG-MING UNIVERSITY, Taipei (TW)

( * ) Notice: Subject to any disclaimer, the term of this patent is extended or adjusted under 35 U.S.C. 154(b) by 564 days.

(21) Appl. No.: 14/681,631

(22) Filed: Apr. 8, 2015

(65) Prior Publication Data

US 2016/0222336 A1 Aug. 4, 2016

(30) Foreign Application Priority Data

Jan. 30, 2015 (TW) .............................. 104103173 A

(51) Int. Cl.
*C12M 1/00* (2006.01)
*C12M 3/06* (2006.01)
*C12M 1/04* (2006.01)

(52) U.S. Cl.
CPC ............ *C12M 23/16* (2013.01); *C12M 23/24* (2013.01); *C12M 29/06* (2013.01); *C12M 29/20* (2013.01)

(58) Field of Classification Search
CPC ...... C12M 23/16; C12M 23/24; C12M 29/06; C12M 29/20
USPC ....................................................... 435/289.1
See application file for complete search history.

(56) References Cited

U.S. PATENT DOCUMENTS

2014/0273187 A1* 9/2014 Johnson ............... G01N 33/492
435/287.2

FOREIGN PATENT DOCUMENTS

WO WO-2008028241 A1 * 3/2008 ............ C12M 23/12
WO WO-2013086505 A1 * 6/2013 ............ B01L 3/5027

* cited by examiner

*Primary Examiner* — Michael L Hobbs
*Assistant Examiner* — Liban M Hassan
(74) *Attorney, Agent, or Firm* — Muncy, Geissler, Olds & Lowe, P.C.

(57) ABSTRACT

The present invention provides a microfluidic bio-reactor device, which comprises: a first cell culture layer; a microfluidic base, which is located on the top of the first cell culture layer; a microfluidic layer, which is located on the top of the microfluidic base and have an air-bubble removal device; a microfluidic roof, which is located on the top of the microfluidic layer; the present invention also provides a method for culturing cells by the microfluidic bio-reactor device of the present invention and the kit with a cell-loading device and present microfluidic bio-reactor device.

15 Claims, 16 Drawing Sheets
(1 of 16 Drawing Sheet(s) Filed in Color)

MICROFLUIDIC BIO-REACTOR DEVICE

CROSS-REFERENCE TO RELATED APPLICATIONS

This Non-provisional application claims priority under 35 U.S.C. § 119(a) on Patent Application No(s). 104103173 filed in Taiwan, Republic of China Jan. 30, 2015, the entire contents of which are hereby incorporated by reference.

FIELD OF THE INVENTION

This invention relates to a cell culture device, which is especially suitable for culturing stem cells. The features of the cell culture device include an open-cover design and an air-bubble removal design. An open-cover design, which achieved by negative pressure, make the cells homogenously distribute onto culture substrate. An air-bubble removal design is used to prevent the air bubbles of culture medium entered the culture chamber, achieving a long-term culture.

BACKGROUND OF THE INVENTION

Cell culture is a very basic and important tool in the bio-medical research field, especially for culturing stem cells. Stem cell plays an important role in living organism from the embryo to the matured organism. Therefore, the potential of stem cell is unlimited in the regenerative medical field. However, in vitro culture environment of stem cell is harsh and the culture technology is also difficult. Moreover, the previous studies found that the cell behavior and properties in conventional culture method are extremely different with the in vivo cells. In order to mass production of cells, an innovative device and method for stably culturing cells is needed.

The microfluidic devices have been utilized in cell culture for many years. However, the shortcomings of the conventional microfluidic device include: (1) Cell injection through seeding microchannels causes uneven cells distribution which affects cellular interaction and therefore influences differentiation; (2) When cell injection is completed during injection processes, some cells still stay in the injection microchannel and may not be properly delivered into the culture chamber. The nutrient of the residual cells near the inlet and microchannel of device is not sufficient, leading to abnormal growth and death, therefore affect the growth of other normal cells; (3) The unhealthy cells and air-bubble could not be removed after loading the cells and culture medium into sealed microfluidic device, so that the growth of other normal cells is affected; (4) the culture chamber area is not big enough or the volume of whole device is too large, which is not conducive to mass production of cells.

SUMMARY OF THE INVENTION

Accordingly, the present invention provides a microfluidic bio-reactor device, which comprising: a first cell culture layer; a microfluidic base, which is located on the top of the first cell culture layer; a microfluidic layer, which is located on the top of the microfluidic base, and a microfluidic roof, which is located on the top of the microfluidic layer. The first cell culture layer is a closed circuit to forming an inside of a first cell culture chamber. The microfluidic base has a first channel, a second channel and holes, wherein the position of the first channel and the second channel are located inside an area corresponding to the inside of the first cell culture chamber, and the position of the holes are located inside an area corresponding to the closed circuit of the first cell culture layer. The microfluidic layer, which comprising: an inlet having a first end and a second end, wherein the first end of inlet is an opening and the second end of the inlet is connected to a curved channel; a first diffusion device having a first end and a second end, wherein the first end of the first diffusion device is connected to the curved channel and the second end of the first diffusion device is connected to an gas permeable layer, and the first diffusion device have an opening which is connected to the first channel of the microfluidic base; an air-bubble removal device, which is a vacuum channel, having a first end and a second end, wherein the first end of the air-bubble removal device is connected to the gas permeable layer and the second end of the air-bubble removal device is connected to a vacuum opening, and the vacuum channel is connected to the holes of the microfluidic base; and an outlet having a first end and a second end, wherein the first end of the outlet is an opening and the second end of the outlet is connected to a second diffusion device, wherein the second diffusion device have an opening which is connected to the second channel of the microfluidic base.

Preferably, the first diffusion device and the second diffusion device of the present device are fan-shaped.

Preferably, the inlet and the outlet of the present device are at the same sides or at opposite sides of the microfiber layer.

Preferably, the first cell culture layer, the microfluidic layer and the gas permeable layer of the present device are polydimethylsiloxane (PDMS). In one of the embodiment, the polydimethylsiloxane (PDMS) was patterned by laser direct writing (LDW) technique ($CO_2$ laser machine, ILS-II, Laser Tools and Techniques, Hsinchu, Taiwan).

Preferably, the thickness of the first cell culture layer and the microfluidic layer of the present device is 100-400 μm.

Preferably, the microfluidic bio-reactor device of the present device further comprises a first cell culture substrate, which is located under the first cell culture layer and the area of the first cell culture substrate is bigger than the area of the first cell culture layer.

Preferably, the microfluidic bio-reactor device of the present invention further used with a cell loading device and an adhesion material.

Preferably, the microfluidic bio-reactor device of the present invention further comprises: a second cell culture layer, which is located on the top of the microfluidic roof; and a second cell culture substrate, which is located on the top of the second cell culture layer. The second cell culture layer is a closed circuit forming an inside of a second cell culture chamber and the area of the second cell culture substrate is bigger than the area of the second cell culture layer. Wherein the microfluidic roof further comprises a third channel, a forth channel and holes, the position of the third channel and the forth channel are located on the inside of the second cell culture chamber relatively, the position of the holes are located on the closed circuit of the second cell culture layer relatively and is connected to the vacuum channel of the microfluidic layer.

Preferably, the second cell culture layer of the present device is polydimethylsiloxane (PDMS).

Preferably, the thickness of the second cell culture layer of the present device is 100-400 μm.

Preferably, the first cell culture substrate and the second cell culture substrate of the present device can be any substrate used for cell culture, such as culture dish, slide, etc.

Preferably, the vacuum opening of the present device is further connected to a vacuum device.

Preferably, the microfluidic base and the microfluidic roof of the present device are glass. In one of the embodiment, the glass was patterned by ultrasonic drilled machine (LUD-1200, Lapidary & Sonic 35 Enterprises, Taipei, Taiwan).

Preferably, the polydimethylsiloxane (PDMS) and the glass of the present device are bonded together by plasma treatment system (PX-250, Nordson, Westlake, Ohio, USA).

Preferably, the first cell culture substrate and the second cell culture substrate of the present device are cut into a specific size by LDW technique ($CO_2$ laser machine, ILS-II, Laser Tools and Techniques, Hsinchu, Taiwan).

Preferably, the microfluidic bio-reactor device of the present invention can further used with a temperature controller, a syringe pump, a flow injection tube, a flow output tube and a vacuum device.

The present invention provides a method for culturing cell by the microfluidic bio-reactor device of the present invention, which comprises: (1) cells are seed on a cell culture substrate evenly; (2) loading the microfluidic bio-reactor device of the present invention on the cell culture substrate to assemble the first cell culture layer of the microfluidic bio-reactor device and the cell culture substrate; (3) connecting the vacuum opening of the microfluidic bio-reactor device with the vacuum device to generate a negative pressure making the first cell culture layer and cell culture substrate adhered tightly; (4) the vacuum device continuously generating negative pressure to maintain the air-bubble removal device as vacuum status; (5) the culture medium inject from the inlet, flow through the opening of the first diffusion device and the first channel of the microfluidic base into the first cell culture layer, wherein the air-bubble in the culture medium would pass the gas permeable layer into the air-bubble removal device; (6) the culture medium in the first cell culture layer would flow through the second channel of the microfluidic base and the opening of the second diffusion device into the outlet.

Preferably, the cell of the present method is stem cell.

The present invention provides a kit for culturing cells, which comprises: a microfluidic bio-reactor device of the present invention; a cell loading device; and an adhesion material.

Preferably, the kit of the present invention further comprises a cell culture substrate.

Preferably, the adhesion material of the present invention is double-sided tape or polydimethylsiloxane (PDMS).

Preferably, the cell loading device of the present invention further comprises a vacuum tube, wherein the vacuum tube connected with a vacuum device to generate a negative pressure to assemble the cell loading device and cell culture substrate.

In summary, the present invention provides a novel microfluidic bio-reactor device, different from the conventional culture device and method known by the skilled in the art, which has the following advantages:
 (1). Culture cells with rapid development time, rapid operation time and large culture chamber, which is suitable for culture stem cells;
 (2). The properties of the cell would not be changed during the cultural process;
 (3). The open-cover design, which achieved by negative pressure, make the cells homogenously distribute onto culture substrate and the unhealthy cells or colonies can be easily removed during the cultural process;
 (4). The air-bubble removal design can ensure long-term cell culture;
 (5). The device can further be used with a cell loading device, which make the cells growth in the specific area, so that the cells will not be damaged or death during the assembling.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 1:
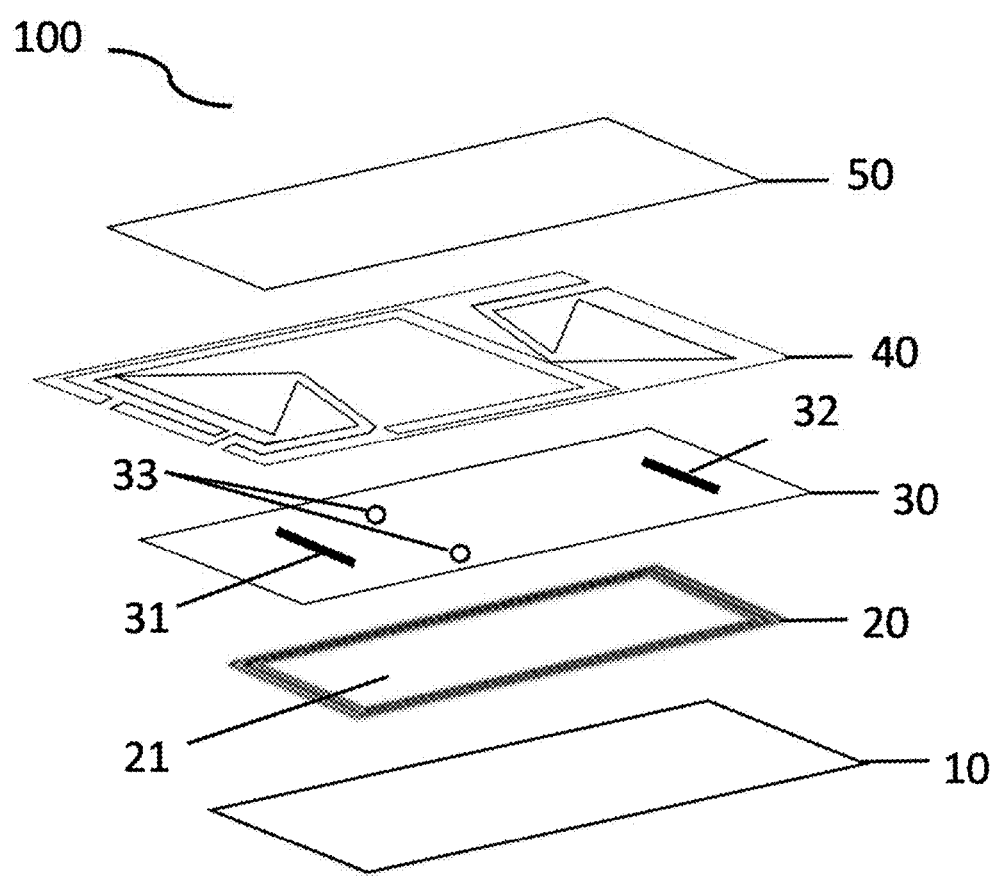
FIG. 1 shows the structure of the present microfluidic bio-reactor device.

SYMBOLS 10 first cell culture substrate
20 first cell culture layer
21 first cell culture chamber
30 microfluidic base
31 first channel
32 second channel
33 holes 40 microfluidic layer
41 inlet
42 outlet
43 vacuum opening
44 curved channel
45 first diffusion device
46 second diffusion device
47 air-bubble removal device
48 gas permeable layer
49 channel
50 microfluidic roof
51 third channel
52 forth channel
53 holes
60 second cell culture layer
61 second cell culture chamber
70 second cell culture substrate
80 cell loading device
81 vacuum tube
90 adhesion material
100 microfluidic bio-reactor device
200 microfluidic bio-reactor device with double culture layer
500 air-bubble

DETAILED DESCRIPTION OF THE INVENTION

Please refer to FIG. 1, the microfluidic bio-reactor device 100 of the present invention comprises: a first cell culture layer 20, which is a closed circuit forming an inside of a first cell culture chamber 21; a microfluidic base 30, which is located on the top of the first cell culture layer 20, having a first channel 31, a second channel 32 and holes 33; wherein the position of the first channel 31 and the second channel 32 are located inside an area corresponding to the inside of the first cell culture chamber 21, and the position of the holes 33 are located inside an area correspond to the closed circuit of the first cell culture layer 20; a microfluidic layer 40, which is located on the top of the microfluidic base 30; and a microfluidic roof 50, which is located on the top of the microfluidic layer 40.

Figure 2:
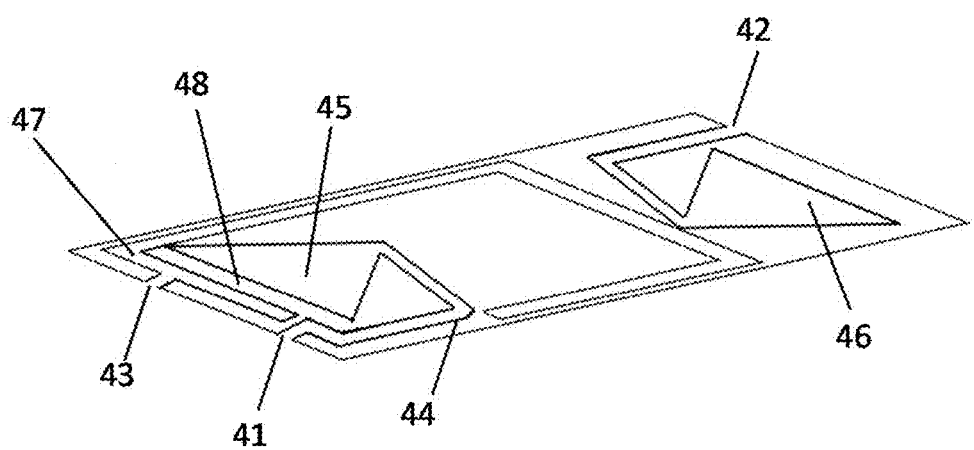
FIG. 2 shows the structure of the microfluidic layer of the present microfluidic bio-reactor device.

Please refer to FIG. 2, the microfluidic layer 40 of the microfluidic bio-reactor device 100 comprising: an inlet 41, wherein one end of inlet is an opening and the other end is connected to a curved channel 44; a first diffusion device 45, wherein one end of the first diffusion device is connected to the curved channel 44 and the other end is connected to an gas permeable layer 48, and the first diffusion device 45 have an opening which is connected to the first channel 31 of the microfluidic base 30; an air-bubble removal device 47, which is a vacuum channel, wherein one end of the air-bubble removal device is connected to the gas permeable layer 48, and the other end is connected to a vacuum opening 43, and the vacuum channel is connected to the holes 33 of the microfluidic base 30; and an outlet 42, wherein one end of outlet is an opening and the other end is connected to a second diffusion device 46, wherein the second diffusion device 46 have an opening which is connected to the second channel 32 of the microfluidic base 30.

In one of the embodiment, the first diffusion device 45 and the second diffusion device 46 of the present microfluidic bio-reactor device 100 are fan-shaped, but not limited.

In one of the embodiment, the inlet 41 and the outlet 42 of the present microfluidic bio-reactor device 100 are at opposite sides, but not limited.

In one of the embodiment, the first cell culture layer 20, the microfluidic layer 40 and the gas permeable layer 48 of the present microfluidic bio-reactor device 100 are polydimethylsiloxane (PDMS), but not limited.

In one of the embodiment, the polydimethylsiloxane (PDMS) was patterned by laser direct writing (LDW) technique ($CO_2$ laser machine, ILS-II, Laser Tools and Techniques, Hsinchu, Taiwan).

In one of the embodiment, the thickness of the first cell culture layer 20 and the microfluidic layer 40 of the present microfluidic bio-reactor device 100 is 100-400 μm.

Please refer to FIG. 1, the microfluidic bio-reactor device 100 of the present invention further comprises a first cell culture substrate 10, which is located under the first cell culture layer 20 and the area of the first cell culture substrate 10 is bigger than the area of the first cell culture layer 20.

In one of the embodiment, the microfluidic bio-reactor device 100 of the present invention further used with a cell loading device and an adhesion material.

Figure 3:
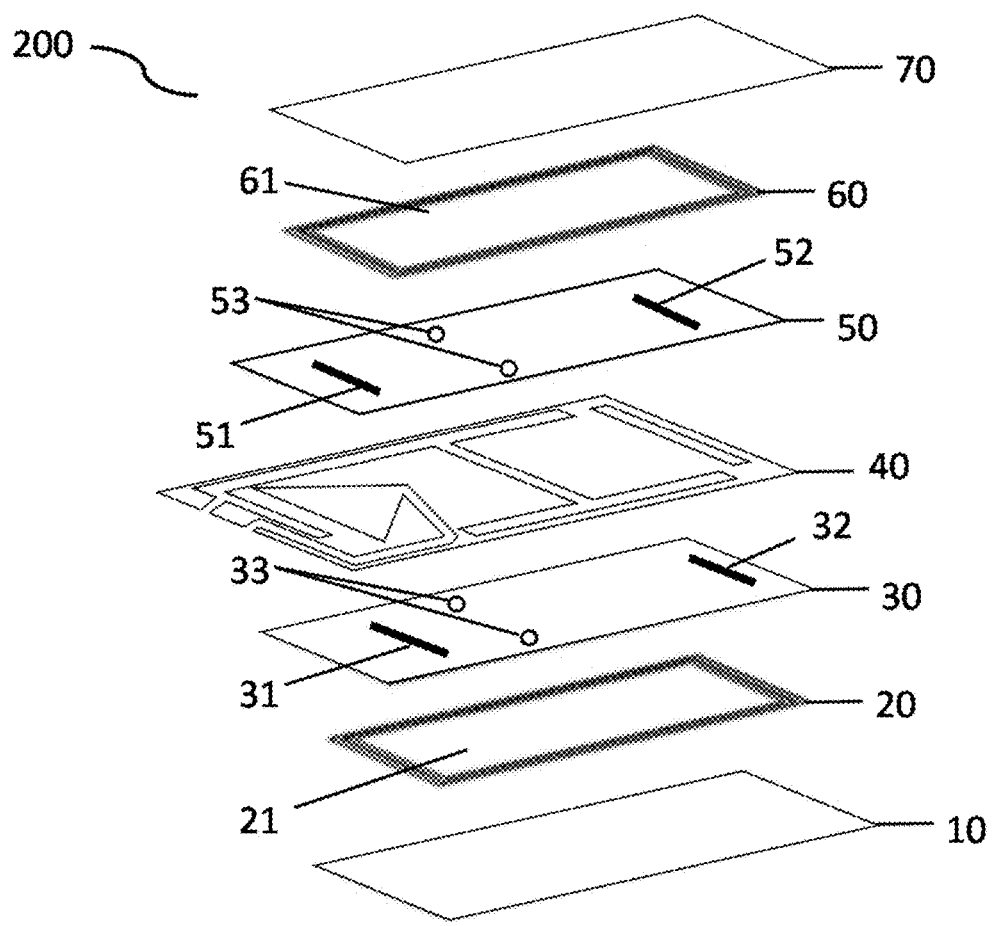
FIG. 3 shows the structure of the present microfluidic bio-reactor device with double culture layer.

Please refer to FIG. 3, the microfluidic bio-reactor device 100 of the present invention further comprises the following structures to form a microfluidic bio-reactor device with double culture layer 200: a second cell culture layer 60, which is located on the top of the microfluidic roof 50, is a closed circuit forming an inside of a second cell culture chamber 61; and a second cell culture substrate 70, which is located on the top of the second cell culture layer 60, and the area of the second cell culture substrate is bigger than the second cell culture layer 60; wherein the microfluidic roof 50 further comprises a third channel 51, a forth channel 52 and holes 53, the position of the third channel 51 and the forth channel 52 are located on the inside of the second cell culture chamber 61 relatively, and the position of the holes 53 are located on the closed circuit of the second cell culture layer 60 relatively and is connected to the vacuum channel of the microfluidic layer 40.

Figure 4:
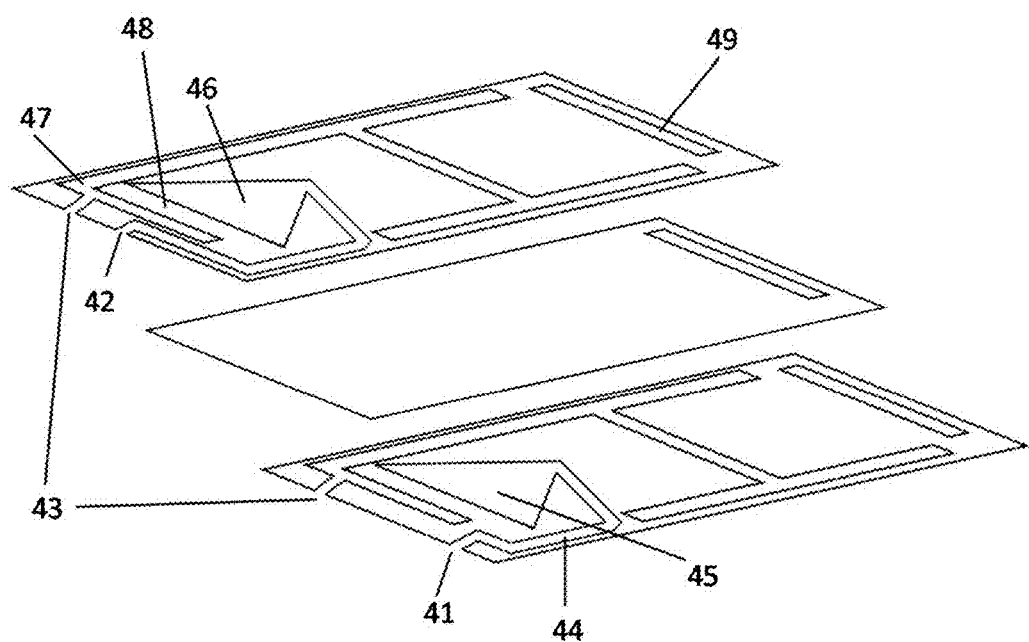
FIG. 4 shows the exploded structure of the microfluidic layer of the present microfluidic bio-reactor device with double culture layer.

In one of the embodiment, the inlet 41 and outlet 42 of the present microfluidic bio-reactor device with double culture layer 200 are at the same side, please refer to FIG. 4. wherein the microfluidic layer 40 further comprises a channel 49, wherein the channel 49 is connected to the second channel 32 of the microfluidic base 30 and the forth channel 52 of the microfluidic roof 50. Therefore, the culture medium in the first cell culture layer 20 would flow through the second channel 32 of the microfluidic base 30, the channel 49 of the microfluidic layer 40, and the forth channel 52 of the microfluidic roof 50 into the second cell culture chamber 60, allowing the culture medium has the best used.

In one of the embodiment, the second cell culture layer 60 of the present microfluidic bio-reactor device with double culture layer 200 is polydimethylsiloxane (PDMS).

In one of the embodiment, the thickness of the second cell culture layer 60 of the present microfluidic bio-reactor device with double culture layer 200 is 100-400 μm.

In one of the embodiment, the first cell culture substrate 10 and the second cell culture substrate 70 of the present invention can be any substrate used for cell culture, such as culture dish, slide, etc.

In one of the embodiment, the vacuum opening 43 of the present invention is further connected to a vacuum device.

In one of the embodiment, the microfluidic base 30 and the microfluidic roof 50 of the present invention are glass.

In one of the embodiment, the glass was patterned by ultrasonic drilled machine (LUD-1200, Lapidary & Sonic 35 Enterprises, Taipei, Taiwan).

In one of the embodiment, the polydimethylsiloxane (PDMS) and the glass of the present invention are bonded together by plasma treatment system (PX-250, Nordson, Westlake, Ohio, USA).

In one of the embodiment, the first cell culture substrate 10 and the second cell culture substrate 70 of the present invention are cut into a specific size by a LDW technique ($CO_2$ laser machine, ILS-II, Laser Tools and Techniques, Hsinchu, Taiwan).

In one of the embodiment, the microfluidic bio-reactor device 100 of the present invention can further used with a temperature controller, a syringe pump, a flow injection tube, a flow output tube and a vacuum device.

The present invention provides a method for culturing cells by the microfluidic bio-reactor device of the present invention, which comprises: (1) cells are seed on a cell culture substrate evenly; (2) loading the microfluidic bio-reactor device of the present invention on the cell culture substrate to assemble the first cell culture layer of the microfluidic bio-reactor device and the cell culture substrate; (3) connecting the vacuum opening of the microfluidic bio-reactor device with the vacuum device to generate a negative pressure making the first cell culture layer and cell culture substrate adhered tightly; (4) the vacuum device continuously generating negative pressure to maintain the air-bubble removal device as vacuum status; (5) the culture medium inject from the inlet, flow through the opening of the first diffusion device and the first channel of the microfluidic base into the first cell culture layer, wherein the air-bubble in the culture medium would pass the gas permeable layer into the air-bubble removal device; (6) the culture medium in the first cell culture layer would flow through the second channel of the microfluidic base and the opening of the second diffusion device into the outlet.

Figure 5:
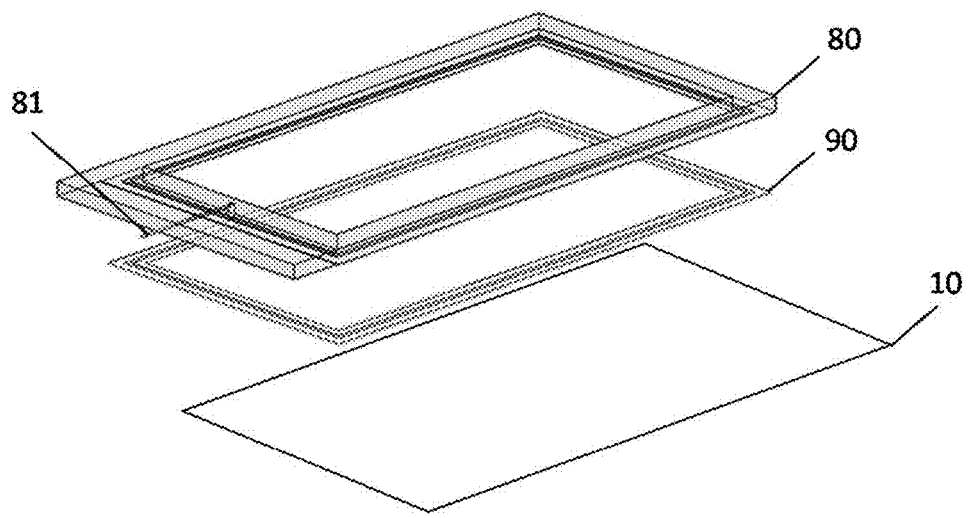
FIG. 5 shows the structure of the cell loading device and the adhesion material.

Please refer to FIG. 5, the present invention provides a kit for culturing cells, which comprises: a microfluidic bio-reactor device 100 of the present invention; a cell loading device 80; and an adhesion material 90.

In one of the embodiment, the kit of the present invention further comprises a cell culture substrate 10.

In one of the embodiment, the adhesion material 90 of the present invention can be double-sided tape or polydimethylsiloxane (PDMS), but not limited.

In one of the embodiment, the cell loading device 80 of the present invention further comprises a vacuum tube 81, wherein the vacuum tube connected with a vacuum device to generate a negative pressure making the cell loading device 80 and cell culture substrate 10 adhered tightly.

The method for culturing cells by the kit of the present invention comprises: (1) assembling the cell loading device 80 and the cell culture substrate 10 by the adhesion material 90; (2) cells are seeded evenly on the cell culture substrate 10 by the conventional culture method and then cells are growth restricted in the area of the cell loading device 80; (3) removing the cell loading device 80; (4) loading the microfluidic bio-reactor device 100 of the present invention on the top of the cell culture substrate 10, and culturing the cells by the method mentioned above.

Figure 6:
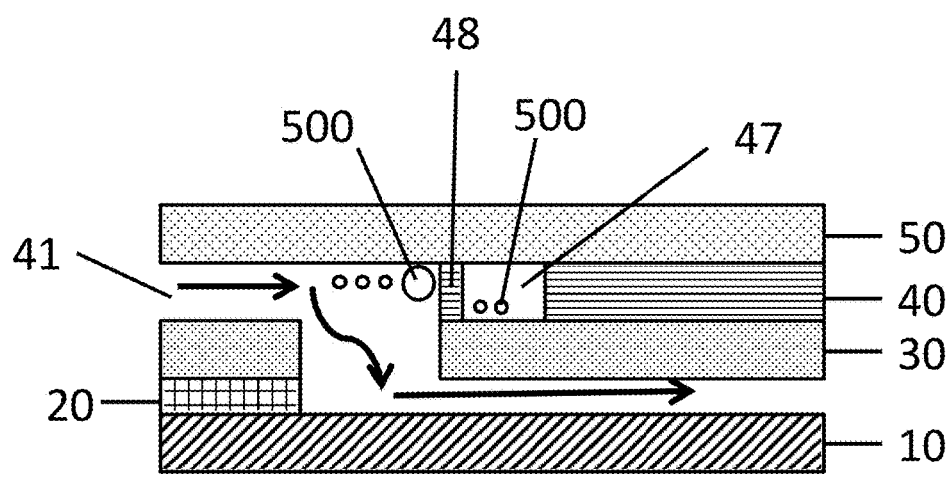
FIG. 6 shows the lateral diagram of the air-bubble removal process of the present microfluidic bio-reactor device.
Figure 7:
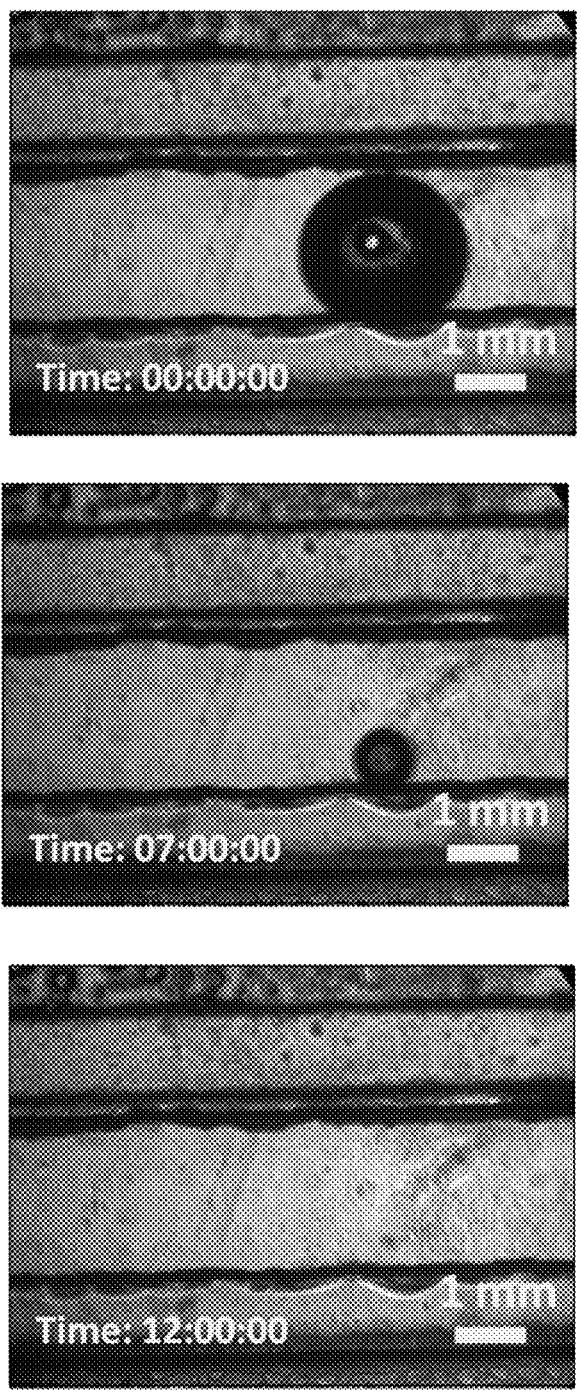
FIG. 7 shows the embodiment of air-bubble removal process in the present microfluidic bio-reactor device.

Please refer to the FIG. 1, FIG. 2 and FIG. 6, the air-bubble removal process of the microfluidic bio-reactor device 100 of the present invention are described as follows: the culture medium inject from the inlet 41 of the microfluidic layer 40, then flows into the first diffusion device 45. The air-bubble 500 would aggregate in the edge of the first diffusion device 45. The gas permeable layer 48 is a gas permeable material (PDMS) allows the air-bubble 500 passing into the air-bubble removal device 47. When vacuuming from the vacuum opening 43, the negative pressure is generated to remove the air-bubble 500 avoid it entering the first cell culture layer 20. Likewise, in the microfluidic bio-reactor device with double culture layer 200 of the present invention, the negative pressure is also generated by the same process to prevent the air-bubble entering the second cell culture layer 60. In one of the embodiment, please refer to the FIG. 7, the air-bubble is disappear gradually from the microfluidic layer 40. The time frame in the FIG. 7 is represented as hours.

EXAMPLE

The culturing result in the microfluidic bio-reactor device of the present invention is showed as following examples:

Example 1, the Cell Properties of Mouse Mesenchymal Stem Cells (MSCs) in the Microfluidic Bio-Reactor Device of the Present Invention Mouse MSCs were harvested from the bone marrow of postnatal 7-week old C57BL/6J mice (National Laboratory Animal Center, Taipei, Taiwan). The mouse MSCs were cultured in the 6-cm culture dish (BD Falcon) and the microfluidic bio-reactor device of the present invention. The mouse MSCs were maintained in Dulbecco's Modified Eagle's Medium (LG-DMEM, Sigma-Aldrich, St. Louis, Mo., USA) and the flow rate was 940 μl/hr.

Figure 8:
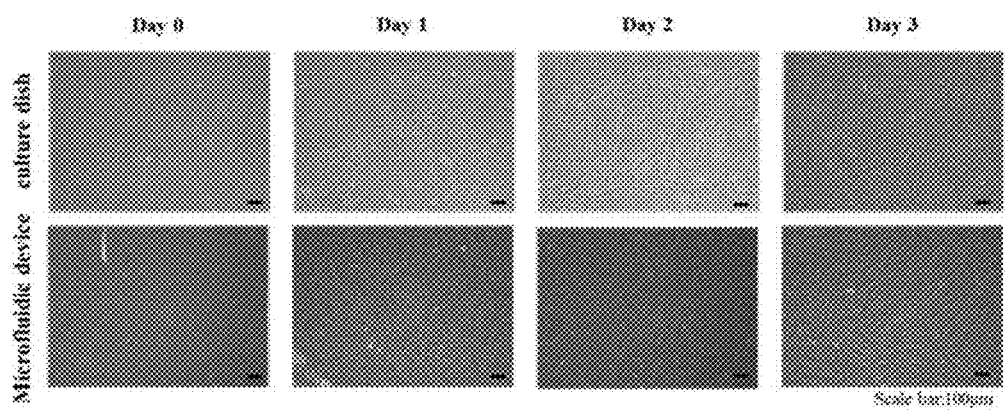
FIG. 8 shows the morphology of the mouse mesenchymal stem cells (MSCs) in the present microfluidic bio-reactor device and the conventional culture dish.
Figure 9:
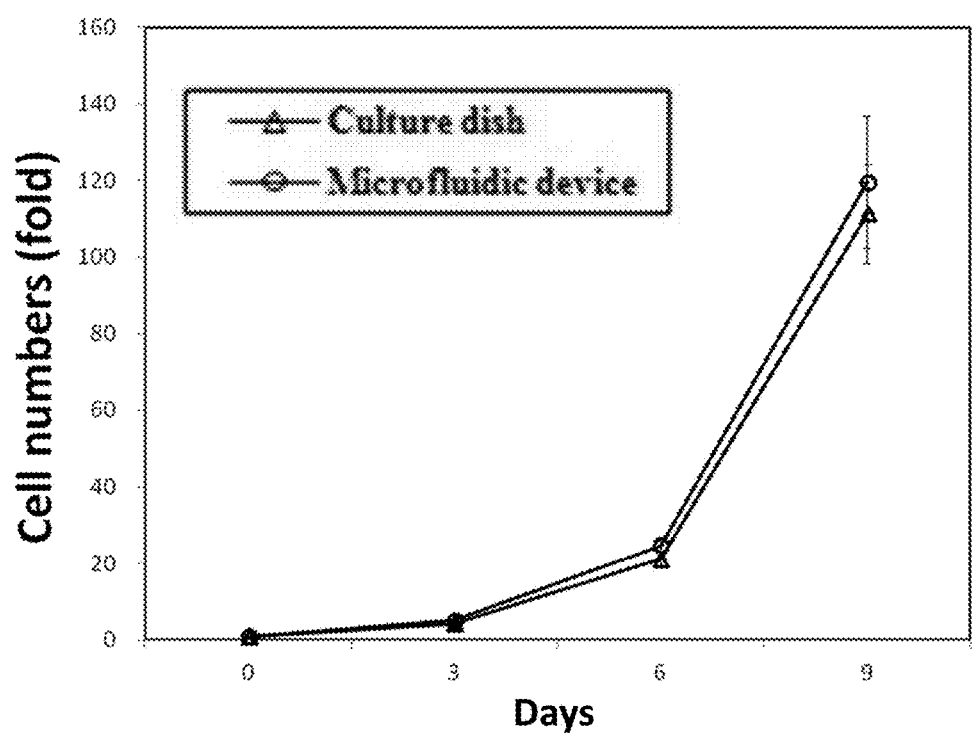
FIG. 9 shows the growth curve of the mouse mesenchymal stem cells (MSCs) in the present microfluidic bio-reactor device and the conventional culture dish.
Figure 10:
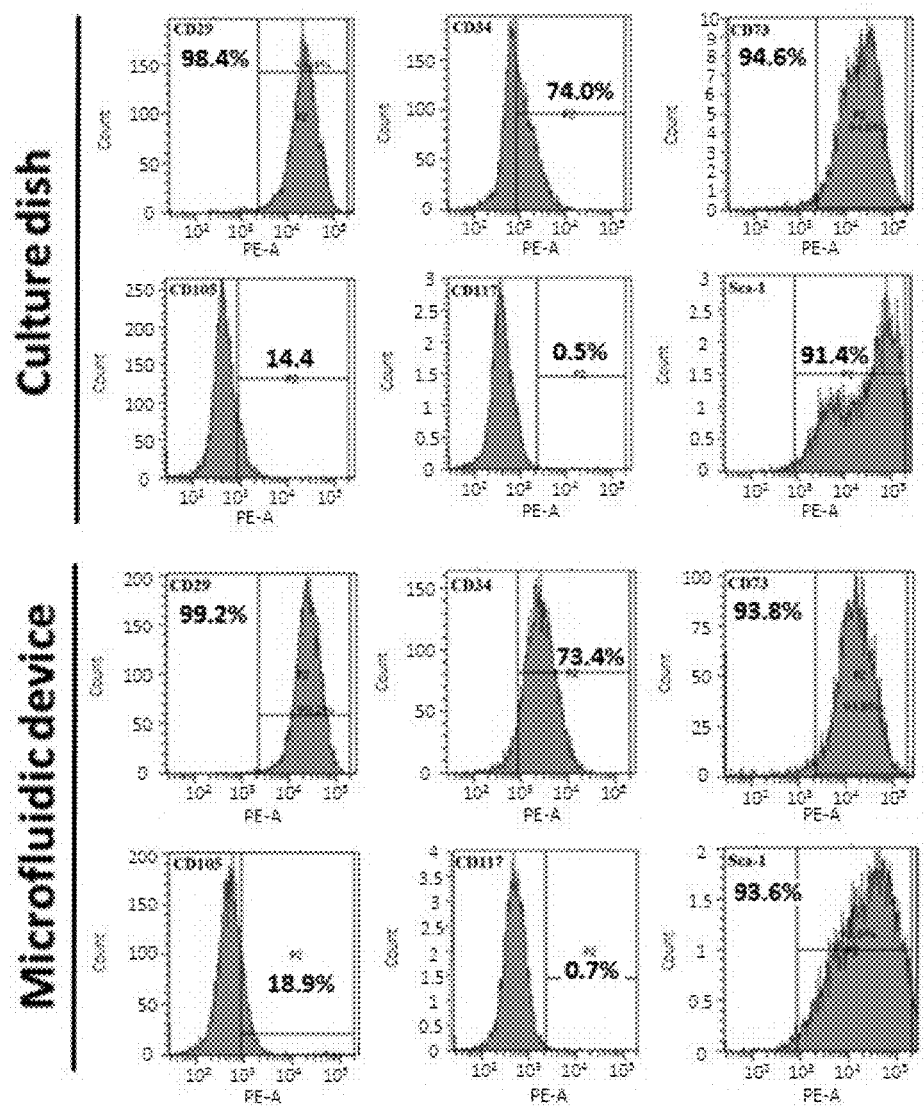
FIG. 10 shows the expressions of cell surface markers of mouse mesenchymal stem cells (mMSCs) in the present microfluidic bio-reactor device and the conventional culture dish.

Please refer to the FIG. 8, the upper row is the result in the 6-cm culture dish and lower row is the result in the microfluidic bio-reactor device of the present invention. In day 0-3, the morphology of the MSCs is similar in both microfluidic bio-reactor device of the present invention and culture dish. Also, as shown in FIG. 9, the growth curve of MSCs is similar in both environments after 9 days of culturing. Further, the expressions of cell surface markers of MSCs in the microfluidic bio-reactor device of the present invention and culture dish were analyzed by flow cytometry. As shown in FIG. 10, the mouse MSCs cultivated in culture dishes and the microfluidic bio-reactor device of the present invention expressed the standard MSC surface markers, such as CD29, CD34, CD73, CD105, CD117, Sca-1. The X-axis in FIG. 10 represents the relative fluorescence intensity and the Y-axis represents cell numbers. This results show that the properties of mouse MSCs cultured in the microfluidic bio-reactor device of the present invention will not be change.

Figure 11:
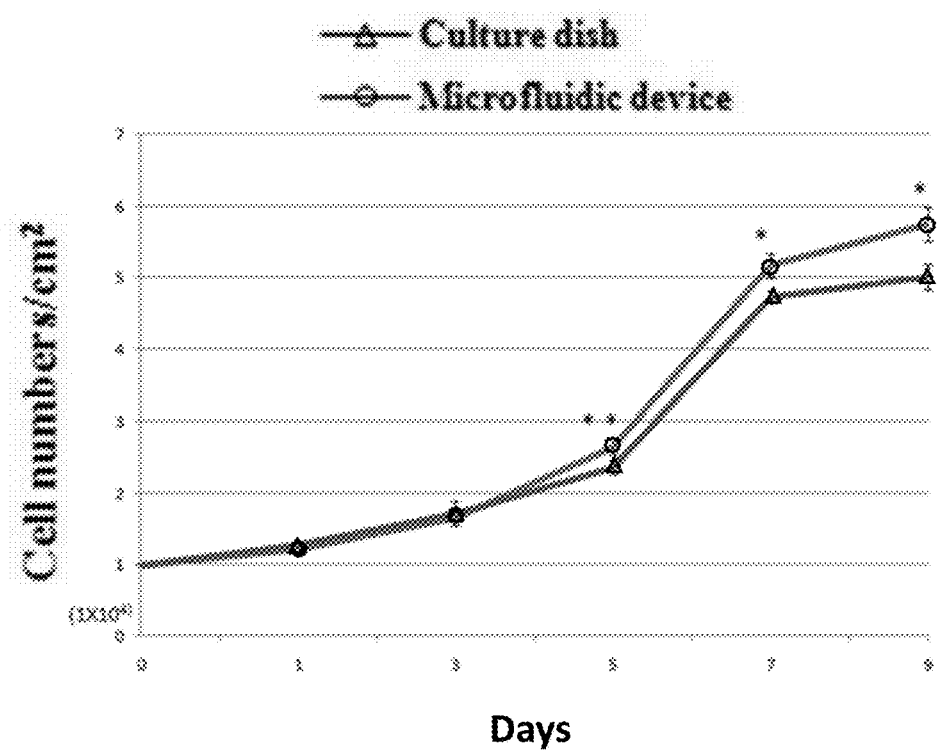
FIG. 11 shows the growth curve of the human mesenchymal stem cells (hMSCs) in the present microfluidic bio-reactor device and the conventional culture dish.
Figure 12:
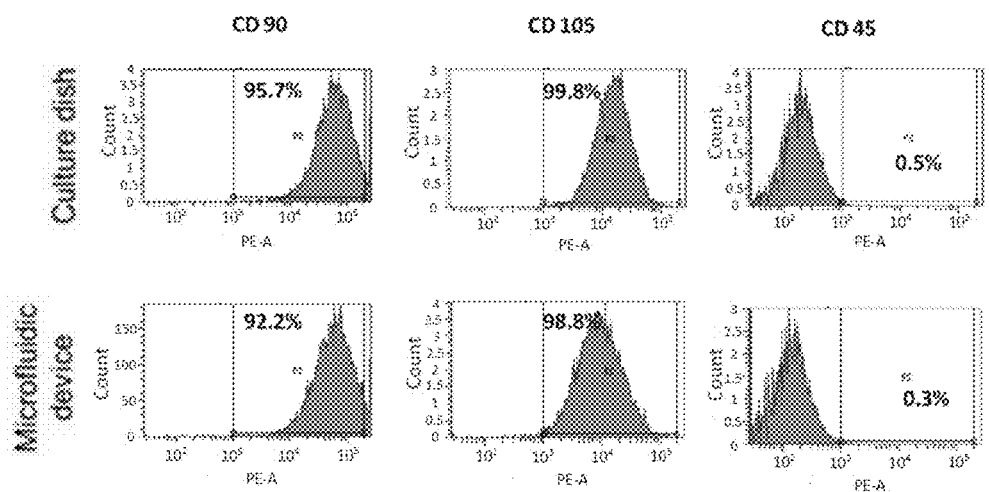
FIG. 12 shows the expressions of cell surface markers of human mesenchymal stem cells (hMSCs) in the present microfluidic bio-reactor device and the conventional culture dish.

Example 2, the Cell Properties of Human Mesenchymal Stem Cells (MSCs) in the Microfluidic Bio-Reactor Device of the Present Invention The human mesenchymal stem cells were purchased from Lonza (Walkersville, Md., #PT-2501). The human MSCs were cultured in the 6-cm culture dish (BD Falcon) and the microfluidic bio-reactor device of the present invention. The human MSCs were maintained in Iscove's modified Dulbecco's medium (IMDM, Gibco BRL, Grand Island, N.Y., USA) and the flow rate is 940 □l/hr. Please refer to FIG. 11, the star sign represents the statistic significant difference. In day 0-9, the growth rate of human MSCs in the microfluidic bio-reactor device of the present invention is better than in the culture dish. Further, the expressions of cell surface markers of human MSCs in the microfluidic bio-reactor device of the present invention and culture dish were analyzed by flow cytometry. As shown in FIG. 12, the human MSCs cultivated in both environments expressed the standard surface markers, such as CD90, CD105, CD45. The X-axis in FIG. 12 represents the relative fluorescence intensity and the Y-axis represents cell numbers. This results show that the properties of human MSCs cultured in the microfluidic bio-reactor device of the present invention will not be change.

Figure 13:
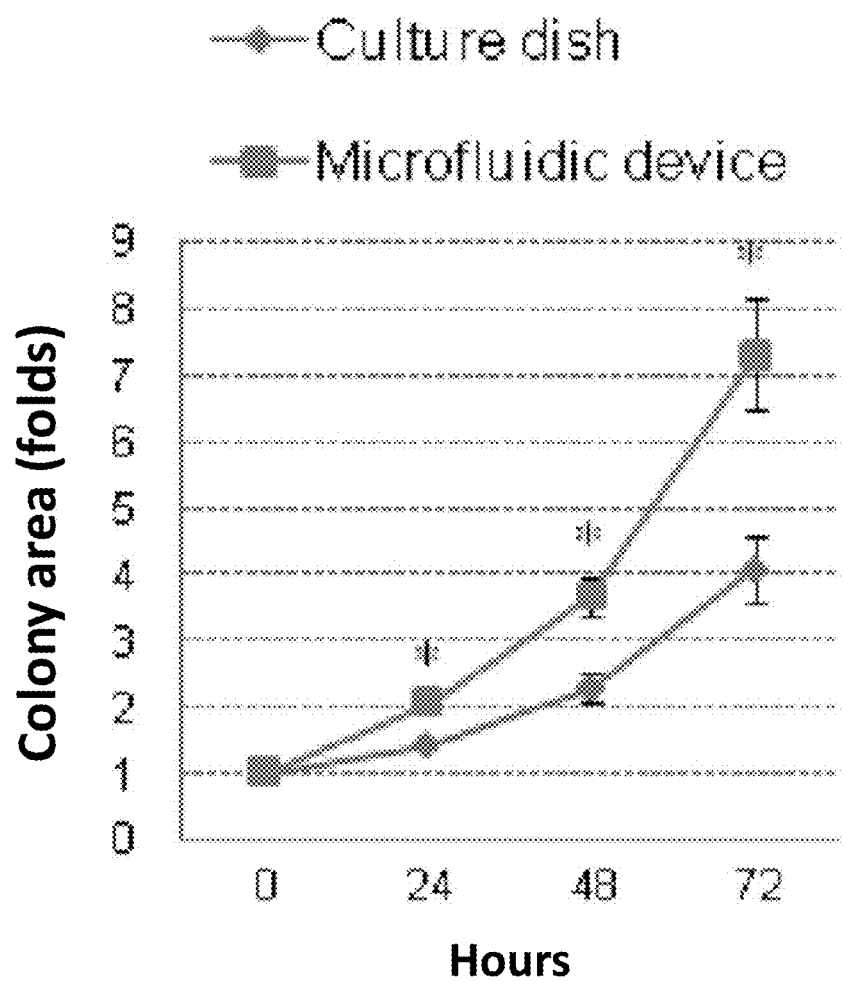
FIG. 13 shows the growth curve of the human embryonic stem cells (ESCs) in the present microfluidic bio-reactor device and the conventional culture dish.
Figure 14:
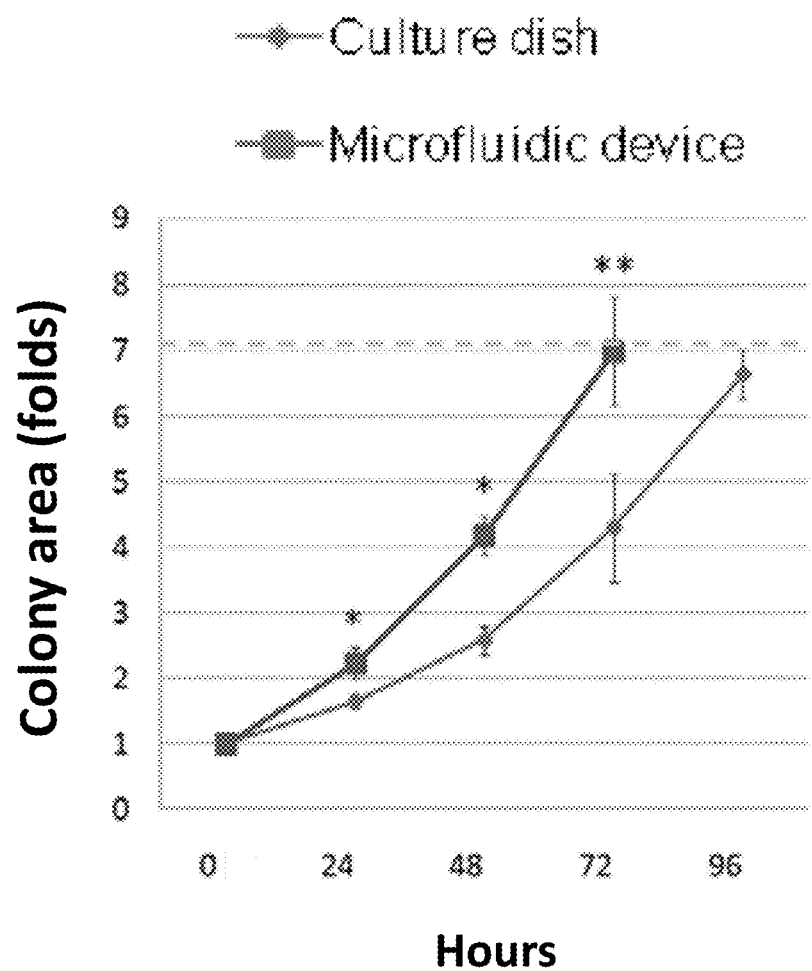
FIG. 14 shows the growth curve of the human induced pluripotent stem cells (iPSCs) in the present microfluidic bio-reactor device and the conventional culture dish.
Figure 15:
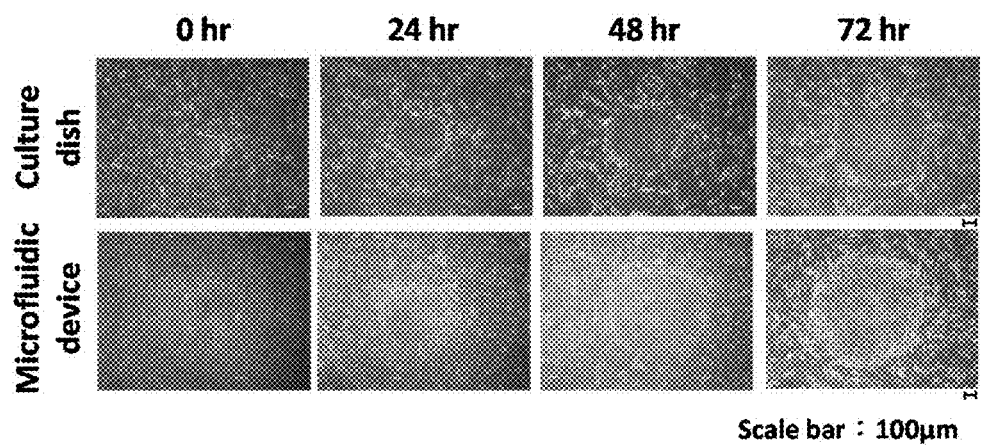
FIG. 15 shows the morphology of the human induced pluripotent stem cells (iPSCs) in the present microfluidic bio-reactor device and the conventional culture dish.
Figure 16:
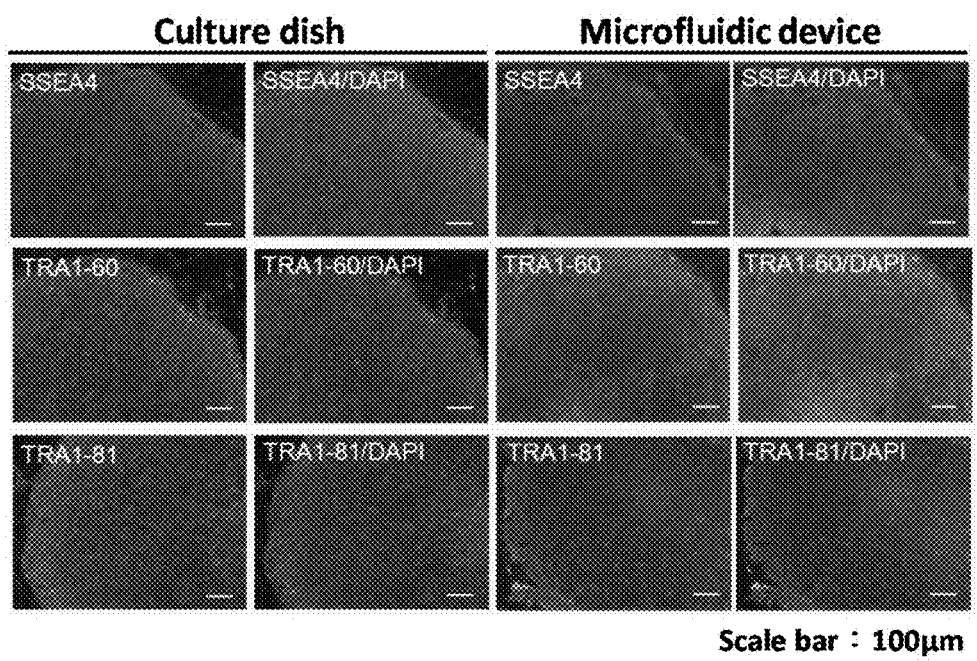
FIG. 16 shows the immune-fluorescence staining analysis of human induced pluripotent stem cells (iPSCs) in the present microfluidic bio-reactor device and the conventional culture dish.

Example 3. The Cell Properties of the Human Embryonic Stem Cells (ESCs) and the Human Induced Pluripotent Stem Cells (iPSCs) in the Microfluidic Bio-Reactor Device of the Present Invention The human embryonic stem cells (ESCs) GE09 (National Institutes of Health, USA) and human induced pluripotent stem cells (iPSCs) CFB46 (Y C. Huang H P, Chen H F, Chen P H, Chuang C Y, Lin S J, "Factors from human embryonic stem cell-derived fibroblast-like) were cultured in the 6-cm culture dish (BD Falcon) and the microfluidic bio-reactor device of the present invention. The human ESCs and iPSCs were maintained in Dulbecco's Modified Eagle's Medium (LG-DMEM, Sigma-Aldrich, St. Louis, Mo., USA) and the flow rate is 1100 µl/hr. Please refer to FIG. 13 and FIG. 14, the star sign represents the statistic significant difference. In day 0-3, the growth rate of the human ESCs (FIG. 13) and the human iPSCs (FIG. 14) in the microfluidic bio-reactor device of the present invention are better than the cells in the culture dish. Besides, as shown in FIG. 15, the morphology of the human iPSCs is similar in both microfluidic bio-reactor device of the present invention and culture dish. Further the fluorescent expressions of the human ESCs in the microfluidic bio-reactor device of the present invention and culture dish were analyzed by immunostaining as shown in FIG. 16. The stage-specific embryonic antigen 4 (SSEA4) and tumor rejection antigen 1-60 & 1-80 (TRA1-60 & 1-81) are the specific cell surface maker of the human iPSCs. DAPI is used to label cell nucleus. These results show that the properties of the human ESCs and the human iPSCs in the microfluidic bio-reactor device of the present invention will not be change.

In summary, the size of the microfluidic bio-reactor device of the present invention can be adjusted depending on the needs. In one of the embodiment, the culture area is 324 cm$^2$ and the relative cell number is about 2×10$^7$ cells. Besides, LDW technique compared with the conventional micro-electro-mechanical techniques can shorten development and fabrication time of the microfluidic device as well as for manufacturing microfluidic device with large-scale culture chamber. The present invention provides a rapid and easy method to manufacture the microfluidic bio-reactor device. The microfluidic bio-reactor device of the present invention device and the cell culture substrate is adhered tightly by negative pressure, achieving an open-cover design, Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

What is claimed is:

1. A microfluidic bio-reactor device comprising:
a first cell culture layer comprising an opening defined by a continuous boundary forming the opening, said first cell culture layer located on a top of a first cell culture substrate, wherein said first cell culture layer and said first cell culture substrate form an inside of a first cell culture chamber;
a microfluidic base, the microfluidic base is located on a top of the first cell culture layer and has a first channel, a second channel and holes, said first channel and said second channel are located inside an area corresponding to the inside of the first cell culture chamber, said holes are located inside an area corresponding to the first cell culture layer;
a microfluidic layer, the microfluidic layer is located on a top of the microfluidic base, and the microfluidic layer comprising:
a gas permeable layer;
a curved channel;
an inlet having a first end and a second end, the first end of the inlet being an opening and the second end of the inlet being connected to the curved channel;
a first diffusion device having a first end and a second end, the first end of the first diffusion device being connected to the curved channel and the second end of the first diffusion device being connected to the gas permeable layer, said first diffusion device has an opening which is connected to the first channel of the microfluidic base;
an air-bubble removal device having a first end and a second end, the air-bubble removal device being a vacuum channel, the first end of the air-bubble-removal device being connected to the gas permeable layer and the second end being connected to a vacuum opening, said vacuum channel is connected to the holes of the microfluidic base;
an outlet having a first end and a second end, the first end of the outlet being an opening and the second end being connected to a second diffusion device, said second diffusion device has an opening which is connected to the second channel of the microfluidic base; and
a microfluidic roof, the microfluidic roof is located on a top of the microfluidic layer.

2. The microfluidic bio-reactor device of claim 1, wherein the first diffusion device and the second diffusion device are fan-shaped.

3. The microfluidic bio-reactor device of claim 1, wherein the inlet and the outlet are at opposite sides of the microfluidic layer.

4. The microfluidic bio-reactor device of claim 1, wherein the first cell culture layer, the microfluidic layer and the gas permeable layer are polydimethylsiloxane (PDMS).

5. The microfluidic bio-reactor device of claim 1, wherein an area of the first cell culture substrate is bigger than the area of the first cell culture layer.

6. The microfluidic bio-reactor device of claim 5, wherein the first cell culture substrate is culture dish or slide.

7. The microfluidic bio-reactor device of claim 1, which further used with an adhesion material and a vacuum tube connected with a vacuum device.

8. The microfluidic bio-reactor device of claim 1, which further comprising:
a second cell culture layer, the second cell culture layer is located on a top of the microfluidic roof and comprising an opening defined by a continuous boundary forming the opening, wherein said second cell culture layer and said microfluidic roof form an inside of a second cell culture chamber; and
a second cell culture substrate, the second cell culture substrate is located on a top of the second cell culture layer, an area of the second cell culture substrate is bigger than an area of the second cell culture layer;

wherein the microfluidic roof further comprises a third channel, a fourth channel and holes, the third channel and the fourth channel are located inside an area corresponding to the inside of the second cell culture chamber, the holes are located on the second cell culture layer, the holes are connected to the vacuum channel of the microfluidic layer.

9. The microfluidic bio-reactor device of claim 8, wherein the second cell culture layer is polydimethylsiloxane (PDMS).

10. The microfluidic bio-reactor device of claim 8, wherein the second cell culture substrate is culture dish or slide.

11. The microfluidic bio-reactor device of claim 1, wherein the vacuum opening is further connected to a vacuum device.

12. A method for culturing cells by microfluidic bio-reactor device comprising:
   (1) seeding cells evenly on the first cell culture substrate of the microfluidic bio-reactor device of claim 1;
   (2) assembling the microfluidic bio-reactor device;
   (3) connecting the vacuum opening of the microfluidic bio-reactor device with a vacuum device to generate a negative pressure making the first cell culture layer and first cell culture substrate adhered tightly;
   (4) the vacuum device continuously generating negative pressure to maintain the air-bubble removal device as vacuum status;
   (5) injecting a culture medium from the inlet, the culture medium flowing through the opening of the first diffusion device and the first channel of the microfluidic base into the first cell culture layer, wherein air-bubble in the culture medium would pass the gas permeable membrane into the air-bubble removal device;
   (6) the culture medium in the first cell culture layer would flow through the second channel of the microfluidic base and the opening of the second diffusion device into the outlet.

13. The method of claim 12, wherein the cells are stem cells.

14. A kit for culturing cells comprising:
   a microfluidic bio-reactor device of claim 1;
   a vacuum tube connected with a vacuum device; and
   an adhesion material.

15. The kit of claim 14, wherein the adhesion material is double-sided tape or polydimethylsiloxane (PDMS).

* * * * *